(12) United States Patent
Latham

(10) Patent No.: US 8,357,278 B2
(45) Date of Patent: Jan. 22, 2013

(54) ELECTROTRANSFER CASSETTE WITH INTEGRATED ELECTRICAL CONTACTS AND LOCKING MECHANISM

(75) Inventor: Matthew Latham, Dixon, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 265 days.

(21) Appl. No.: 12/963,417

(22) Filed: Dec. 8, 2010

(65) Prior Publication Data

US 2011/0297544 A1     Dec. 8, 2011

Related U.S. Application Data

(60) Provisional application No. 61/381,653, filed on Sep. 10, 2010, provisional application No. 61/285,277, filed on Dec. 10, 2009.

(51) Int. Cl.
*G01N 27/447* (2006.01)
*G01N 27/453* (2006.01)
*E05C 1/12* (2006.01)

(52) U.S. Cl. ............................ 204/464; 204/614; 292/34

(58) Field of Classification Search .......... 204/462–464, 204/613, 614; 292/34, 39
See application file for complete search history.

(56) References Cited

U.S. PATENT DOCUMENTS

| | | | | |
|---|---|---|---|---|
| 533,298 A * | 1/1895 | Hollar | ............................. | 292/39 |
| 995,712 A * | 6/1911 | Pcikering | ........................... | 220/7 |
| 1,179,099 A * | 4/1916 | Hayashi | ........................... | 292/39 |
| 5,094,483 A | 3/1992 | James | | |
| 5,112,459 A * | 5/1992 | Sorge et al. | .................... | 530/427 |
| 5,189,768 A | 3/1993 | Riceman et al. | | |
| 6,193,868 B1 | 2/2001 | Hsu | | |
| 6,955,382 B2 * | 10/2005 | Eggum | ......................... | 292/116 |
| 2004/0195103 A1 | 10/2004 | Zhou | | |
| 2008/0157541 A1 * | 7/2008 | Olsen | .............................. | 292/34 |

* cited by examiner

*Primary Examiner* — Alex Noguerola
(74) *Attorney, Agent, or Firm* — Kilpatrick Townsend & Stockton LLP.; M. Henry Heines

(57) ABSTRACT

An electrotransfer cassette is formed in two parts that are releasably joined by a manually operated locking mechanism. The joined parts have electrical contact areas extending from the electrodes in the two parts of the cassette, the contact areas being exposed on an outer edge of the resulting cassette to form electrical connections to a power supply upon the simple insertion of the cassette into an instrument.

16 Claims, 9 Drawing Sheets

ELECTROTRANSFER CASSETTE WITH INTEGRATED ELECTRICAL CONTACTS AND LOCKING MECHANISM

CROSS-REFERENCE TO RELATED APPLICATION

This application claims the benefit of U.S. Provisional Patent Application No. 61/285,277, filed Dec. 10, 2009, and of U.S. Provisional Patent Application No. 61/381,653, filed Sep. 10, 2010. The contents of both of these provisional applications are incorporated herein by reference.

BACKGROUND OF THE INVENTION

1. Field of the Invention

This invention resides in the field of gel electrophoresis, and relates in particular to the transfer of electrophoretically separated species from a slab gel in which the species were separated to a sheet-form support matrix in which the species can be detected, identified, and quantified.

2. Description of the Prior Art

Proteins, nucleic acids, or other biological species that have been electrophoretically separated in a slab gel are often transferred to a membrane of nitrocellulose, nylon, polyvinyl difluoride, or similar materials for identification and quantification which are more easily performed on the membrane than in the gel. A common transfer technique is electroblotting, in which the flat surfaces of the gel and membrane are placed in direct contact and an electric current is passed through both the gel and the membrane in a transverse direction, thereby transferring the species in a manner similar to that by which the species were mobilized within the gel. When the species are DNA fragments, the transfer is termed a Southern blot after its originator, the British biologist Edwin M. Southern. By analogy, the transfer of RNA fragments is termed Northern blotting, and the transfer of proteins or polypeptides is termed Western blotting. Once transfer has occurred, the species on the membrane are analyzed by methods appropriate to the species themselves. In Southern and Northern blots, for example, the analysis involves treatment of the species on the membrane with a hybridization probe, followed by labeling them with a fluorescent or chromogenic dye. In Western blots, the species are treated with antibodies, followed by the use of conventional labeling techniques to detect the antibodies.

Electroblotting of the Southern, Northern, and Western types can all be performed in either a wet, dry, or semi-dry format. In wet blotting, the gel and membrane are layered over each other in a stack which is immersed in a transfer buffer solution in a tank on whose walls are mounted wire or plate electrodes. The electrodes are then energized to cause the solutes to migrate from the gel to the membrane. In semi-dry blotting, filter papers wetted with the transfer buffer solution are used, and the stack contains the filter papers on the top and bottom with the gel and the membrane between the filter papers to form a "blotting sandwich." The electrodes are then placed in direct contact with the exposed surfaces of the wetted filter papers. Dry electroblotting uses no liquid buffers other than those residing in the gels. Descriptions of wet, dry, and semi-dry electroblotting and the associated materials and equipment are found in Margalit et al. (Invitrogen) United States Patent Application Publication No. US 2006/0278531 A1, published Dec. 14, 2006; Littlehales (American Bionetics) U.S. Pat. No. 4,840,714, issued Jun. 20, 1989; Dyson et al. (Amersham International) U.S. Pat. No. 4,889,606, issued Dec. 26, 1989; Schuette (Life Technologies, Inc.), U.S. Pat. No. 5,013,420, issued May 7, 1991; Chan et al. (Abbott Laboratories), U.S. Pat. No. 5,356,772, issued Oct. 18, 1994; Camacho (Hoefer Scientific Instruments), U.S. Pat. No. 5,445,723, issued Aug. 29, 2005; Boquet (Bertin & Cie), U.S. Pat. No. 5,482,613, issued Jan. 9, 1996; and Chen (Wealtec Enterprise Co., Ltd.) U.S. Pat. No. 6,592,734, issued Jul. 15, 2003.

SUMMARY OF THE INVENTION

The present invention resides in an electrotransfer cassette of unique construction. The term "electrotransfer cassette" is used herein to mean any receptacle that contains electrodes and can accommodate a gel or other medium that has chemical or biological species distributed therein in a two-dimensional array such as the wells of a microtiter plate, plus a membrane or other two-dimensional matrix to which the species are to be transferred by the influence of the electric field generated by the electrodes. While broad in application, the cassettes of this invention are of particular value for use in semi-dry electroblotting. The cassette construction includes a top part and a bottom part, with the two electrodes in the form of flat plates mounted on the top and bottom parts, respectively. The anode is preferably in the bottom part and the cathode in the top part, although the reverse arrangement, with the cathode in the bottom part and the anode in the top part, is a functional alternative. For convenience, however, the top part will be referred to herein as the cathode support and the bottom part as the anode support. In all locations where the term "cathode support" is used, it is understood that the cathode plate in that support can be replaced by an anode plate, and vice versa for the term "anode support."

The cathode and anode supports are readily secured together and readily removed from each other by a locking and releasing mechanism that is manually operable from the cathode support. The mechanism includes pegs that extend laterally from opposing side edges of the cathode support and that are aligned with apertures in raised walls of the anode support. The pegs are movable between extended positions where the pegs protrude through the corresponding apertures and retracted positions where the pegs are withdrawn into the cathode support and out of engagement with the apertures. The former is a locking position in which the cathode and anode supports are secured together by way of the extended pegs and the engagement of the extended pegs by the apertures. The latter is a release position in which the cathode and anode supports can be separated from each other, or placed in contact prior to being locked in place by the pegs. Movement of the pegs is achieved by a finger grip that can be manipulated by a single hand of the user and that shifts the positions of all pegs simultaneously between the two positions. In preferred embodiments, as explained below, the finger grip is a rotary disk in the cathode support that is joined to the pegs through any conventional mechanical connection that translates rotary motion to linear motion. An example is a rack-and-pinion gear, where a toothed circular gear fixed to the rotary disk engages toothed bars on two sides, where each bar is an extension of a frame or web to which the pegs are mounted. Rotation of the circular gear causes the bars and hence the frames and pegs to move simultaneously in opposite directions, i.e., outward for the pegs to protrude through the apertures or inward to withdraw from the apertures, depending on the direction of rotation of the circular gear. The locations of the apertures in the raised walls of the anode support of the cassette fix the height of the cathode support above the anode support, and hence the distance between the cathode and the anode. The pegs and apertures also hold the electrodes parallel to each other. Alternatives to the rotary disk will be readily apparent to those skilled in the art. One alternative is a pair of spring-loaded finger tabs that can be grasped between the user's thumb and forefinger, squeezed together to retract the pegs, and released to extend the pegs.

Further features of the cassette in preferred embodiments of the invention include a two-portion cathode (i.e., upper electrode) support in which the electrode plate is affixed to a lower portion and the rack-and-pinion mechanism is mounted to an upper portion. In these embodiments, the upper and lower portions are joined by mating members in a snap-on connection of variable but spring-loaded separation to allow the electrode plate to be raised or lowered to accommodate blotting sandwiches of different thicknesses. In certain embodiments as well, the cassette contains anodic and cathodic electrical contacts that are accessible from the exterior of the cassette for electrical connection to a power supply. In preferred embodiments, the electrical connections to these contacts are made by simple contact, such as upon insertion of the cassette into an instrument with internal power connections. Still further features in preferred embodiments of the invention are integrated gasket features that isolate, or maintain a separation between, the interior surfaces of both the top and bottom portions of the cassette, on one hand, and the gel and membrane or other blotting materials, on the other. These gasket features preserve the structural materials of the cassette from the chemical deterioration that might otherwise result from contact with the chemicals in the gel and the buffers. Still further features will be apparent from the descriptions that follow and the accompanying figures.

DETAILED DESCRIPTION OF THE INVENTION AND PREFERRED EMBODIMENTS

Figure 1:
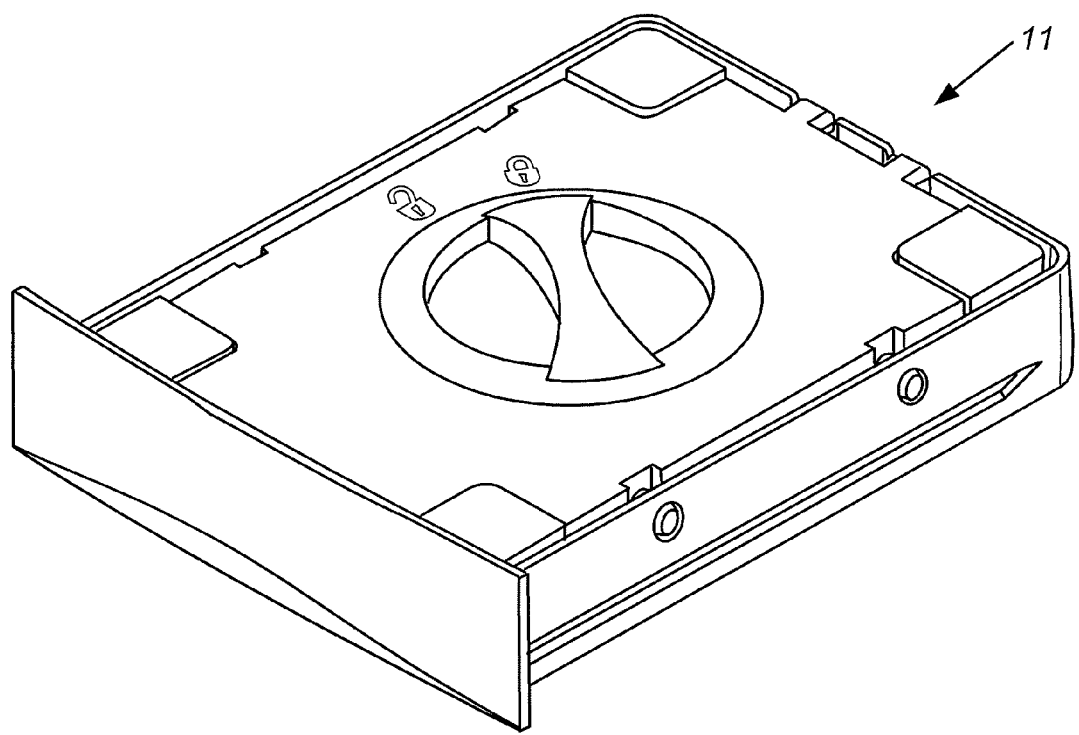
FIG. 1 is a perspective view of an example of a cassette in accordance with the present invention.

The perspective view in FIG. 1 depicts one example of an assembled cassette 11 within the scope of this invention, while the separated cathode support 12 and anode support 13 are depicted in the succeeding Figures. The cathode support 12 is shown from above in FIG. 2A and from below in FIG. 2B. The anode support 13 is shown from above in FIG. 3A and from below in FIG. 3B. Both supports are rectangular in shape; the anode support 13 has raised walls 14, 15, 16, 17 on all four sides to receive the cathode support 12 in a close but loose fit so that the cathode support 12 can easily be inserted inside these walls and removed. The cathode and anode themselves are visible in FIGS. 2B and 3A, respectively, the anode 21 residing on the floor of the anode support (FIG. 3A) and the cathode 22 on the underside of the cathode support (FIG. 2B).

The anode support 13 has an integrated gasket 23 (FIG. 3A), which can be overmolded onto the floor of the support. The gasket extends around the periphery of the floor of the anode support and encircles the anode 21. The blotting sandwich is placed on the anode inside the gasket 23. When the cathode and anode supports are joined, the cathode 22 (FIG. 2B) contacts the upper surface of the blotting sandwich. A raised ridge 24 (FIG. 2B) is formed on the underside of the cathode support. The raised ridge 24 can be formed of additional gasket material overmolded onto the cathode support. Although they do not contact each other, the gasket 23 and the raised ridge 24 prevent the chemicals in the blotting sandwich from contacting parts of the cassette other than the anode and cathode. Gases generated during the blotting process can pass from the cassette through the gap between the gasket 23 and the raised ridge 24 to escape the cassette through the gaps between the long edges of the cathode support and the long side walls of the anode support.

Figure 2A:
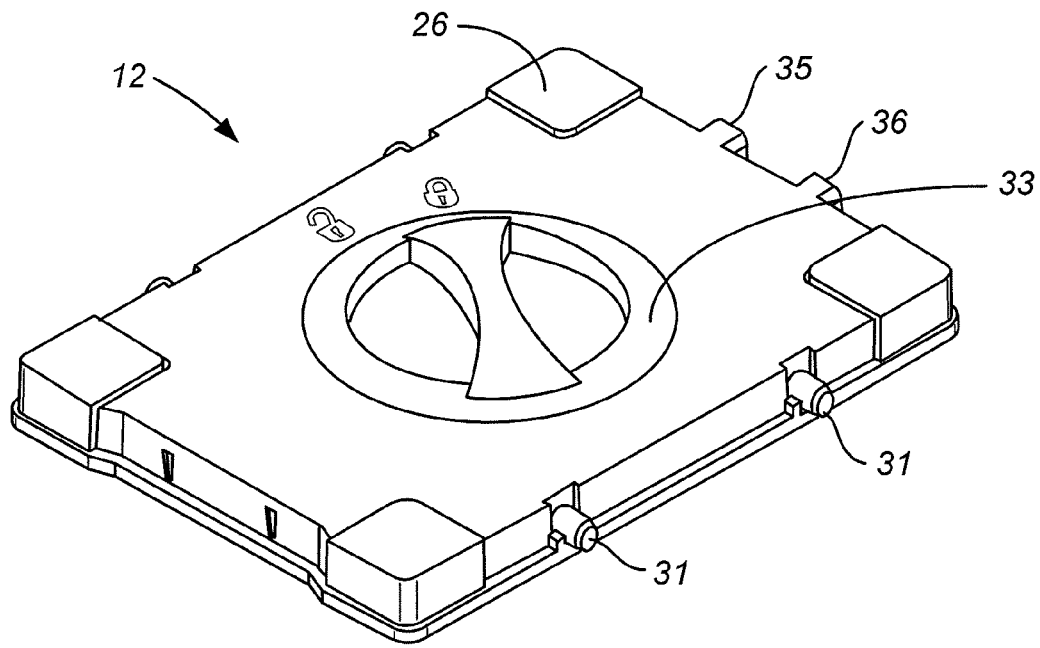
FIGS. 2A and 2B are top and bottom views, respectively, of the cathode support of the cassette of FIG. 1, showing the movable pegs.
Figure 2B:
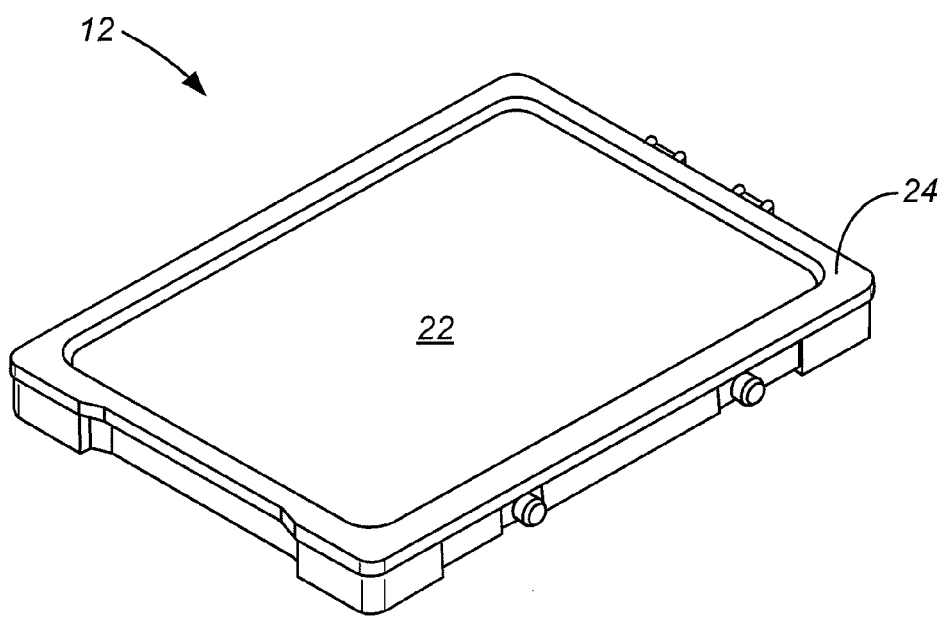

Further features of the cathode and anode supports are overmolded feet 25 on the underside of the anode support (FIG. 3B), and similarly overmolded corner pads 26 on the four corners of the upper surface of the cathode support (FIG. 2A). The feet 25 are useful in stabilizing the cassette on a laboratory bench. The corner pads 26 help center the cathode support in the anode support and facilitate the insertion of the cassette into the instrument. The movable pegs 31 (FIG. 2A) are part of the cathode support 12, which contains two pairs of such pegs, one pair on each of the two longer side edges of the top part, extending outward. The apertures 32 (FIG. 3A) that receive the pegs are in the raised walls along the two longer side edges of the anode support. The rotary disk 33 that governs the positions of the pegs is integrated into the cathode support 12 (FIG. 2A), and discussed in more detail below.

The pegs are preferably oriented with their axes parallel to the cathode plate, and their motion when shifting between the locking and release positions is along these axes. In the embodiment shown, the cathode and anode supports are both rectangular in outline, each having a pair of opposing parallel side edges on their longest sides. The locations of the pegs are not critical provided that they maintain the anode and cathode plates in a parallel relation when securing the two supports together. Preferably, therefore, at least one peg resides on each of the two parallel side edges, more preferably two or more on each side, as shown.

Figure 3A:
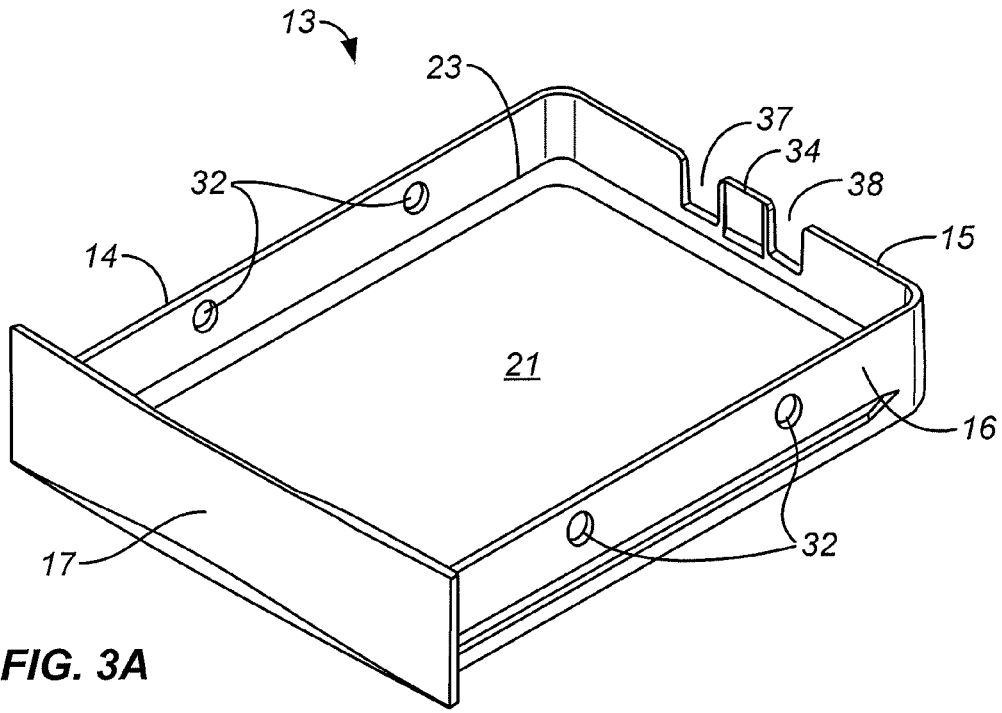
FIGS. 3A and 3B are top and bottom views, respectively, of the anode support of the cassette of FIG. 1.
Figure 3B:
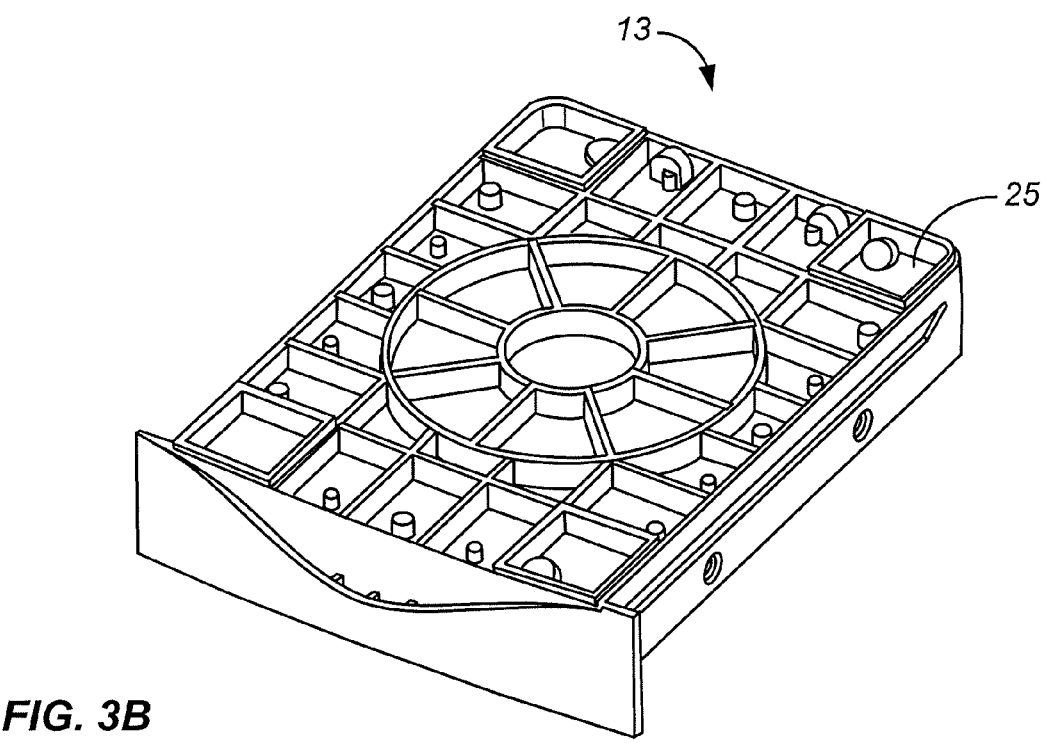
Figure 4:
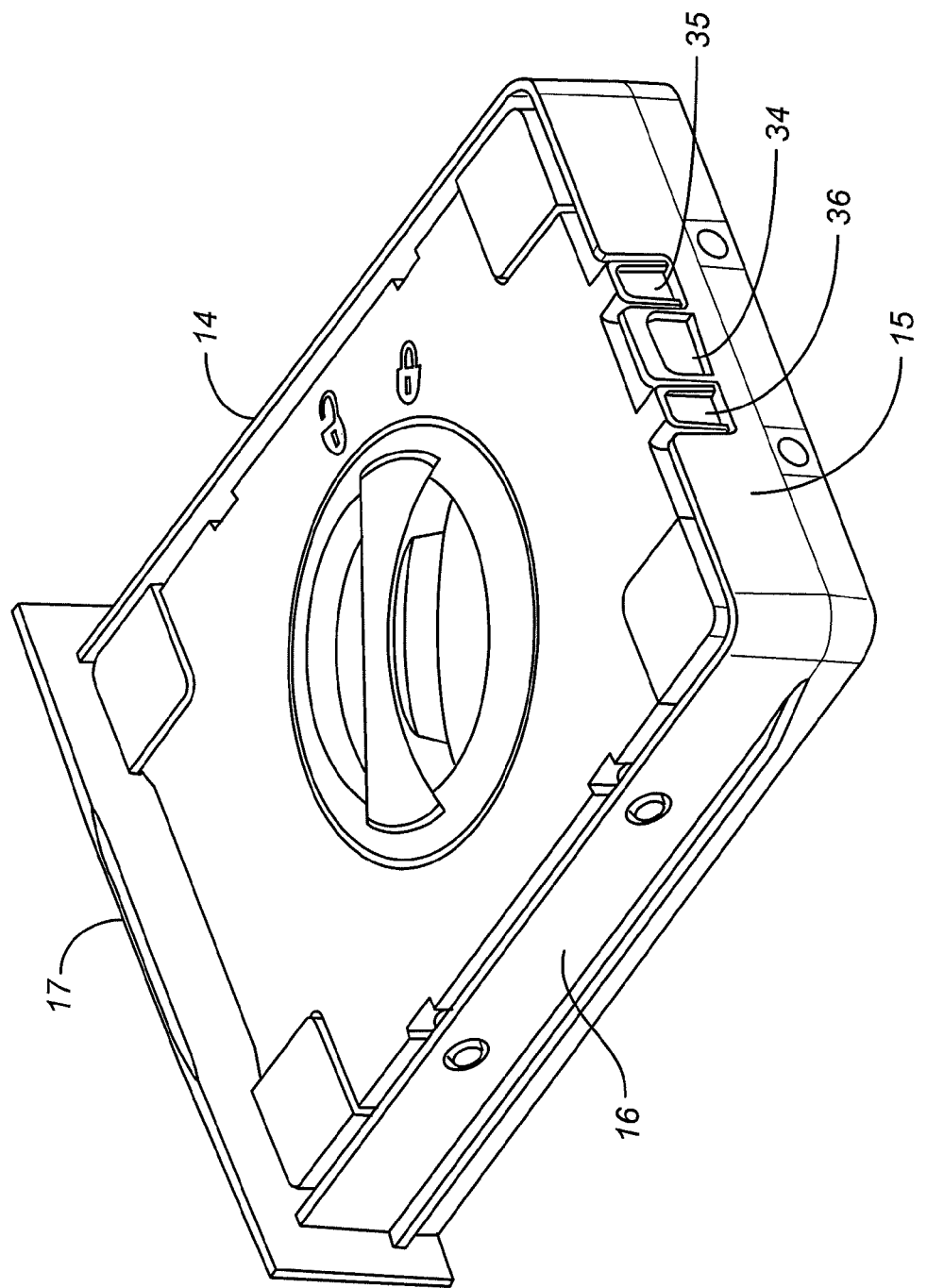
FIG. 4 is a perspective view of the cassette of FIG. 1 from the rear.

External contacts for the cathode and anode plates reside in the cathode and anode supports of the cassette, respectively, in one end wall of each support. Referring to FIG. 3A, a flat area on the outer surface of the back end wall 15 serves as a single anode contact 34. Referring to FIG. 2A, two protrusions 35, 36 with flat ends extending outward from the back edge of the cathode support serve as cathode contacts. The contacts are extensions of the anode and cathode plates, respectively, bent to a vertical position. When the cathode and anode supports are joined, the two protrusions 35, 36 protrude through slots 37, 38 in the back wall 15 of the anode support (FIG. 3A), so that all three contacts are exposed at the back edge of the assembled cassette and are substantially coplanar, as shown in FIG. 4. All of the contacts can thus be energized simultaneously by insertion of the cassette into an instrument that has correspondingly positioned internal contacts. The particular shapes and arrangement of the cathode and anode contacts shown in these Figures are designed for redundancy, with an anode contact that is wide enough to engage two corresponding contacts in the instrument, and with two cathode contacts, likewise to engage two contacts in the instrument. Alternate arrangements that will function similarly are those with a single contact for the anode and a single contact for the cathode, or with a single elongated contact for the cathode and two contacts for the anode. Likewise, as mentioned above, the anode and cathode can be reversed, with the anode can be in the top part of the cassette and the cathode in the bottom part and the external contacts reversed correspondingly.

In the embodiment shown in FIGS. 1, 2A, 2B, 3A, and 3B, control of the height of the cathode above the anode and the parallel spacing between them is achieved by features on the floor of the anode support adjacent to the front end wall 17 (FIG. 3A, although the features are not visible in the drawing) and by heights of the bottoms of the slots 37, 38 in the back end wall 15 as the cathode support 12 rests on these features and slots.

Figure 5:
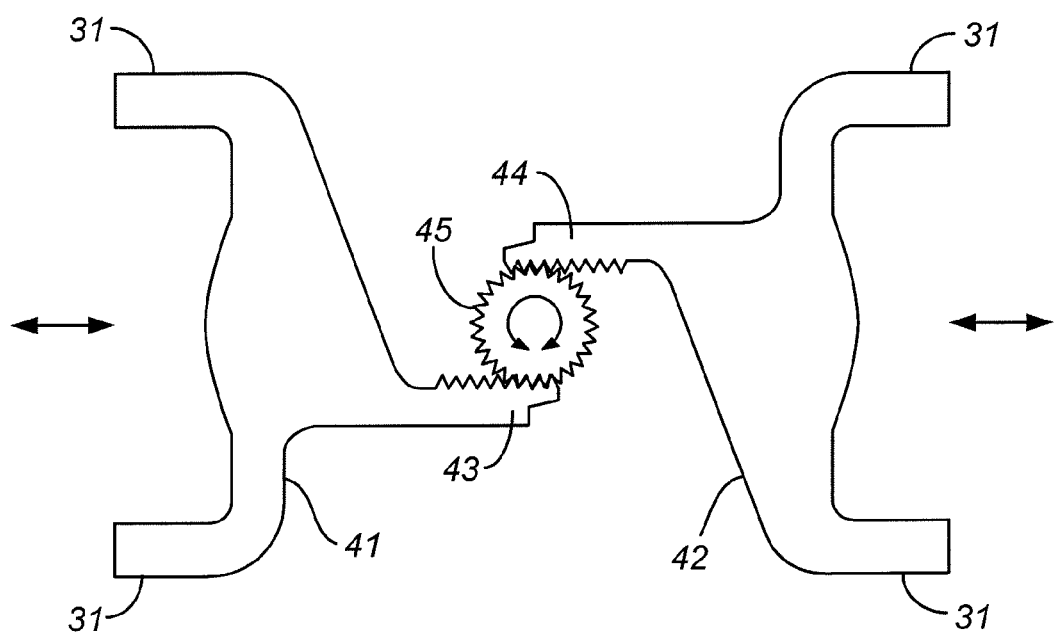
FIG. 5 is a plan view of the rack-and-pinion mechanism for locking and releasing the cassette of FIG. 1.
Figure 6A:
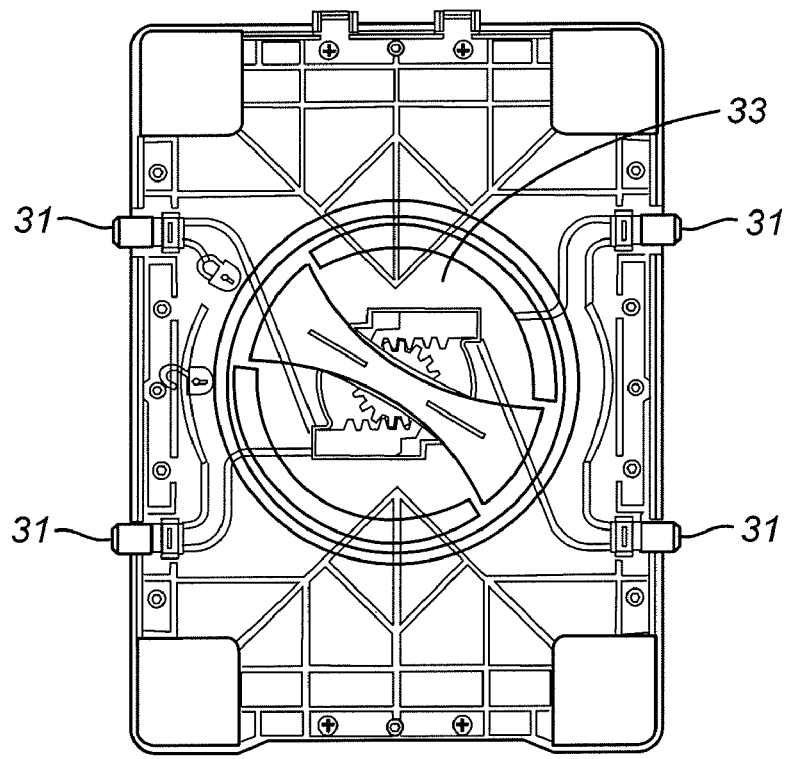
FIGS. 6A and 6B are views of the two positions, respectively, of the rack-and-pinion mechanism of the cassette of FIG. 1.
Figure 6B:
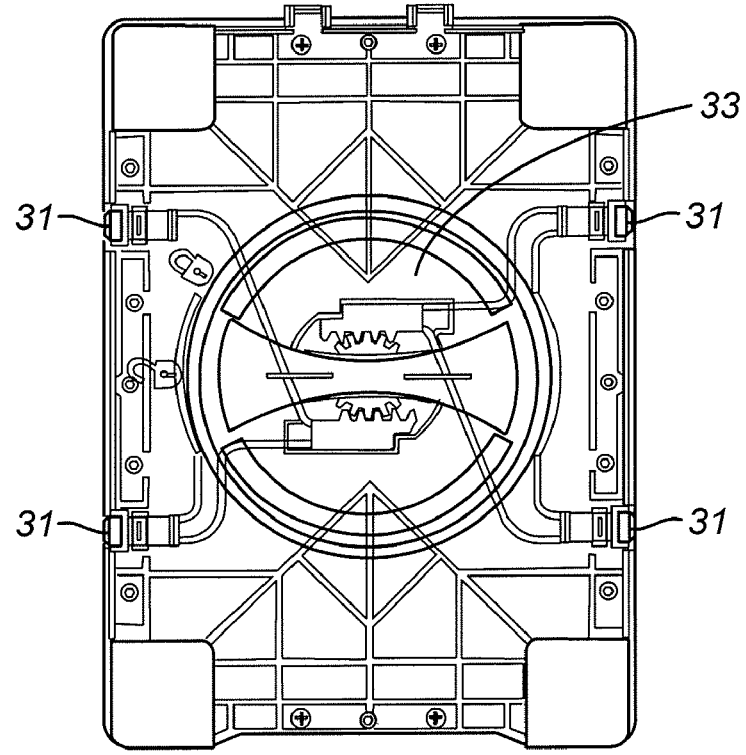

The rack-and-pinion mechanism governing the positions of the pegs 31 is shown in FIG. 5. The pegs are extremities of frames, the four pegs thus being part of two frames 41, 42. At the inner end of each frame is a toothed bar 43, 44, the two sets of teeth (one set on each bar) engaging opposite sides of a circular gear 45. Rotation of the circular gear in one direction thus causes both frames to move outward, and hence both pairs of pegs to protrude further outward, and rotation in the other direction causes both frames, and hence both pairs of pegs, to move inward. The circular gear 45 is affixed to the underside of the rotary disk 33. FIGS. 6A and 6B are horizontal cross sections of the cathode support, showing the action of the rotary disk and moving the pegs. The locking position is shown in FIG. 6A and the release position is shown in FIG. 6B.

Figure 7:
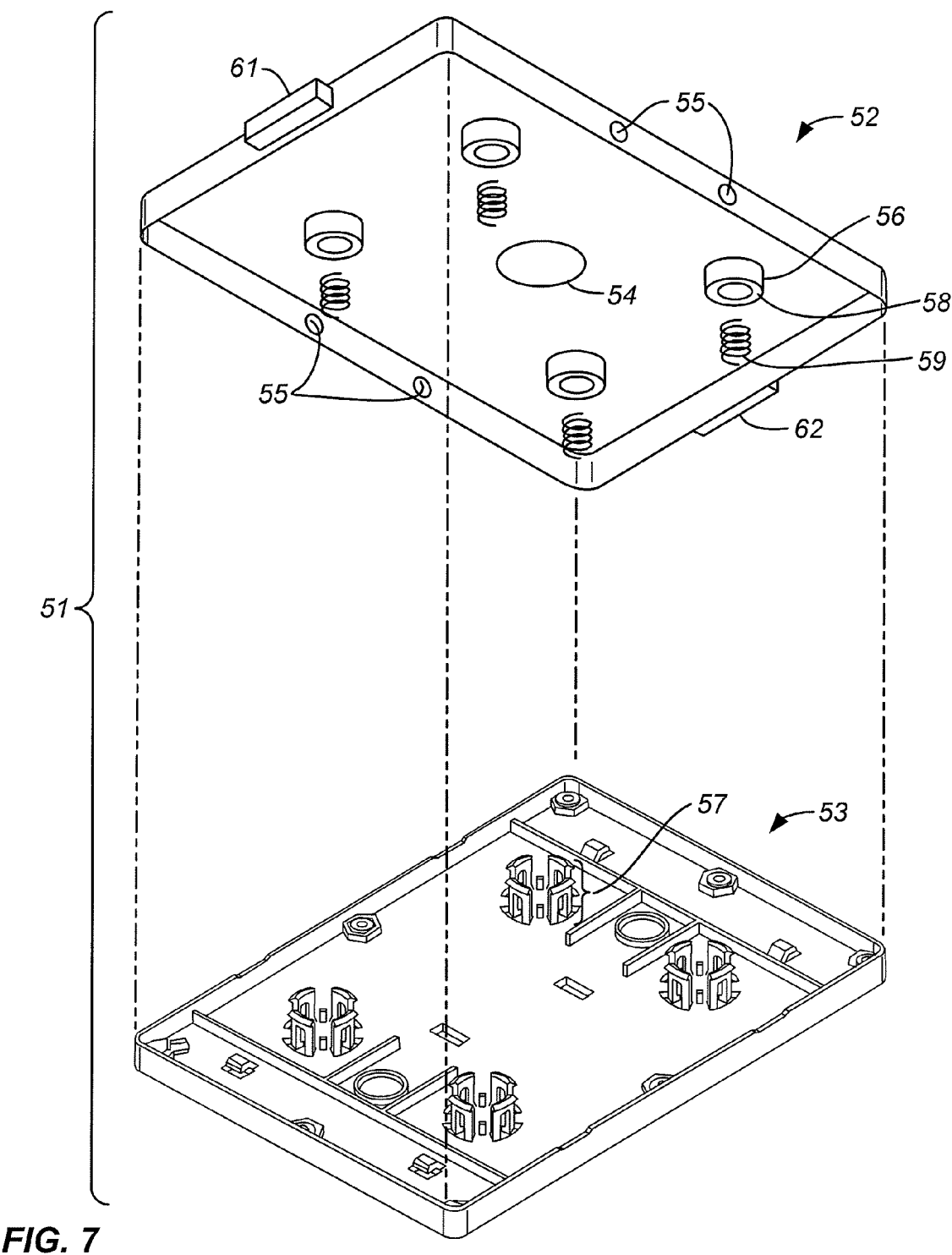
FIG. 7 is an exploded view of an alternative cathode support of a cassette within the scope of this invention, the cathode support itself being formed in two portions.
Figure 8:
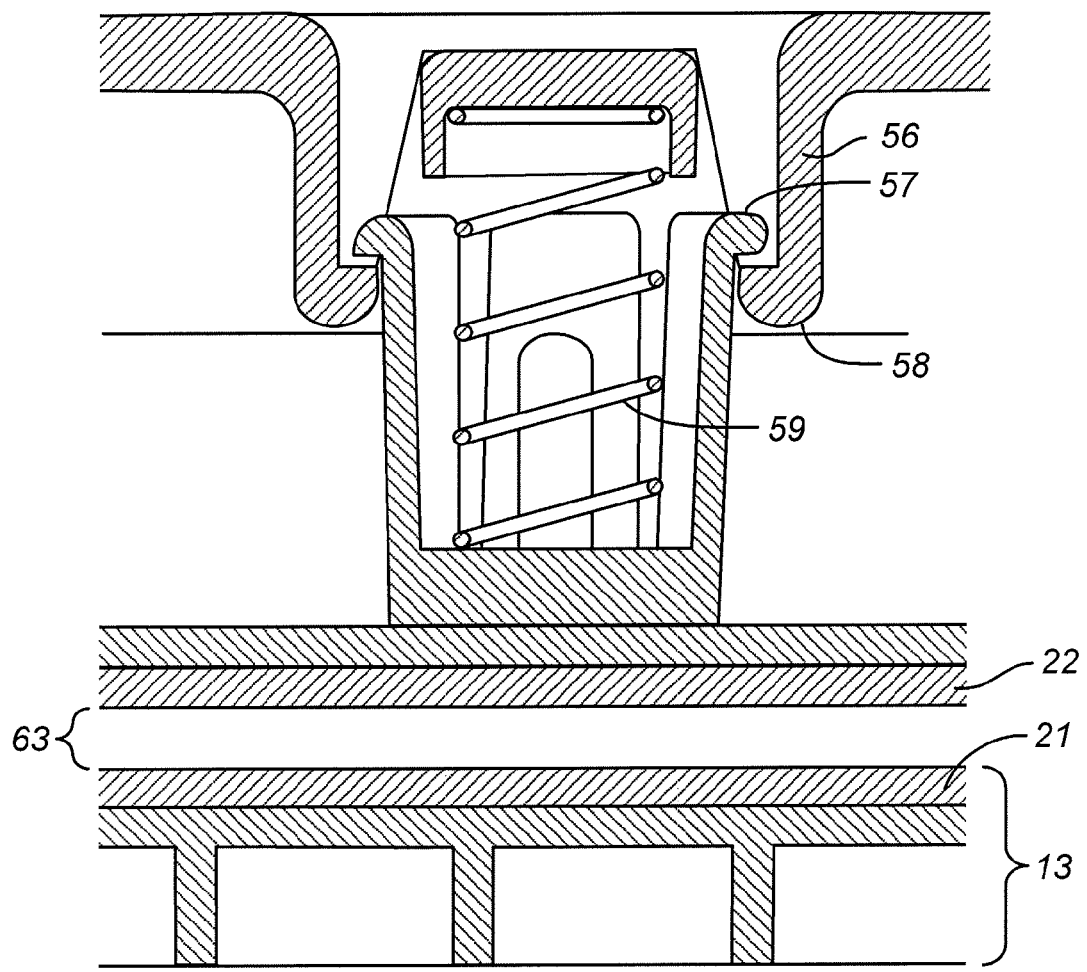
FIG. 8 is a cross section of a segment of a cassette using the alternative cathode support of FIG. 7.
Figure 9:
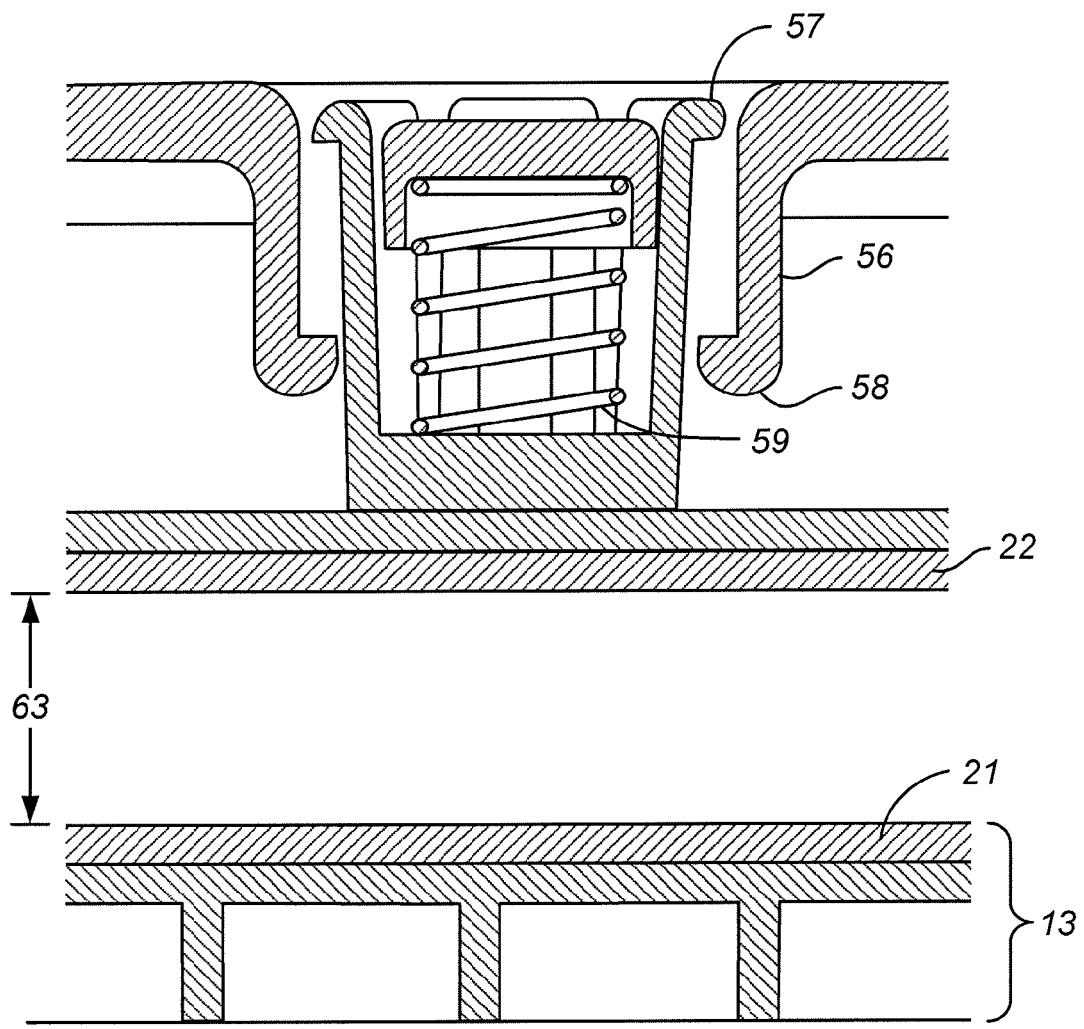
FIG. 9 is a view of the same cross section as FIG. 8, expanded to accommodate a thicker blotting sandwich.

An alternative cassette with added features is depicted in FIGS. 7, 8, and 9. FIG. 7 depicts the cathode support 51 of the cassette, the cathode support itself being formed in two portions, a shell 52 and an electrode plate mount 53 with the shell fitting over the mount. A cathode plate (not visible) is secured to the underside of the electrode plate mount 53 analogously to the cathode plate of the structures of the preceding Figures. A rack-and-pinion mechanism, although not shown in FIG. 7, is secured to the underside of the shell 52 at the location of the circle 54, and has the same structure as that shown in FIG. 5. The movable pegs 31 (FIG. 5) that extend from the rack-and-pinion mechanism pass through lateral apertures 55 in the shell to engage the lateral apertures 32 (FIG. 3A) in the bottom part of the cassette. The shell 52 and electrode plate mount 53 of the cathode support 51 shown in FIG. 7 are joined together by four pairs of mating members, each mating pair consisting of a hollow boss or shell 56 extending downward from the upper portion 52 and a set of resiliently mounted hooks 57 extending upward from the lower portion 53. Each set of hooks consists of four hooks with arcuate cross sections, arranged in a circle. Each hollow boss 56 terminates in a widened rim 58 or inverse flange (with a lip extending toward the center axis of the boss), and the hooks 57 face outward. The hollow bosses 56 are aligned with the hooks 57 and when the parts are joined, each hollow boss 56 fits over a corresponding set of four hooks 57 and all four hooks snap into place to engage the rim 58 of the boss. Spring-loaded biasing members can be included to contact both the shell and the electrode plate mount to urge the plate mount downward from the shell and yet to allow the plate mount to be pushed upward upon contact with the blotting sandwich to accommodate a relatively thick blotting sandwich between the two electrode plates. The spring-loaded biasing members are represented by a coil spring 59 inside each boss 56.

Also shown in FIG. 7 are electrical contacts 61, 62, protruding from opposing edges of the upper portion 52 corresponding to the cathode contacts 35, 36 in the structure shown in FIG. 4. The placement of the contacts 61, 62 on opposing edges allows the cassette to be inserted into an instrument in either direction.

Since the movable pegs protruding laterally from the cathode support of the cassette in the FIG. 7 embodiment are at a fixed height relative to the upper portion 52 of the cathode support and the apertures 32 are at a fixed height in the anode support (FIG. 3A), the lower portion 53 of the cathode support (i.e., the portion to which the cathode plate is mounted) is the only part that is movable when the cassette is fully assembled, and the position of the lower portion 53, and hence the height of the cathode plate, determine the vertical distance between the cathode plate and the anode plate. The height self-adjusts to accommodate the thickness of the blotting sandwich. When assembling the cassette over a blotting sandwich, therefore, the user places the blotting sandwich over the anode on the bottom part of the cassette, then places the top part of the cassette over the blotting sandwich and presses down on the top part, compressing the springs, until the pegs are aligned with the apertures in the bottom part. For a thick blotting sandwich, the pressure on the cathode plate from below causes compression of the springs 59, while for a thin blotting sandwich, the springs are relatively relaxed.

Two conditions of the springs and thus two heights of the cathode plate are shown in FIGS. 8 and 9, respectively. Both Figures are cross sections of a portion of the assembled cassette with a blotting sandwich between the anode and cathode plates, the portion shown being that which is in the immediate vicinity of one of the pairs of mating members joining the two portions of the cathode support. In FIG. 8, the parts shown include a hollow boss 56 with a inwardly-extending rim 58, three of the set of four hooks 57 (two in cross section), the coil spring 59, the cathode plate 22, and the anode support 13 which includes an anode plate 21. The blotting sandwich (also not shown) has been placed between the cathode and anode supports and fills the gap 63 between the cathode plate 22 and the anode plate 21, setting the height of the gap as the spring 59 urges the cathode plate against the top of the blotting sandwich. In FIG. 9, a thicker blotting sandwich is placed between the cathode and anode supports so that when the movable pegs in the cathode support are aligned with the apertures in the anode support to secure the cassette together, the blotting sandwich presses the cathode plate 22 upward against the springs 59. As shown, the spring 59 is compressed and the gap 63 is wide enough to accommodate the thicker blotting sandwich.

Further alternatives to the structures, shapes, and arrangements shown in the figures that are still within the concept of the present invention include contact surfaces that are other than flat, different numbers of movable pegs, different arrangements and locations of the pegs on the cassette rectangle, and other variations that will be readily apparent to those skilled in the art.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is not excluded from the scope of the claim. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. An electrotransfer cassette comprising an upper portion to which a first plate electrode is mounted and a lower portion to which a second plate electrode is mounted, electrical contacts extending from said first and second plate electrodes and exposed on an outer surface of said cassette, and a releasable locking mechanism for securing said upper portion to said lower portion with said first and second plate electrodes parallel, said releasable locking mechanism comprising:

a plurality of pegs movably mounted to said upper portion to move between a locking position in which said pegs engage said lower portion and a release position in which said pegs do not engage said lower portion and said upper and lower portions are free to be separated, and a finger grip mounted to said upper portion, movable by a single hand of a user to shift all of said plurality of pegs simultaneously between said locking position and said release position.

2. The electrotransfer cassette of claim 1 wherein each peg of said plurality of pegs has an axis that is parallel to said first plate electrode and moves along said axis between said locking position and said release position.

3. The electrotransfer cassette of claim 2 wherein said upper portion has a pair of opposing parallel side edges and said plurality of pegs comprise pegs protruding laterally from both said side edges when in said locking position.

4. The electrotransfer cassette of claim 3 wherein said lower portion has raised parallel side edges with apertures positioned to receive said pegs when said pegs are in said locking position.

5. The electrotransfer cassette of claim 1 wherein said finger grip is rotatable between a first angular position in which said plurality of pegs are in said locking position and a second angular position in which said plurality of pegs are in said release position.

6. The electrotransfer cassette of claim 3 wherein said finger grip moves pegs on opposite side edges in opposite directions by a rack-and-pinion mechanism and is rotatable between a first angular position in which said plurality of pegs are in said locking position and a second angular position in which said plurality of pegs are in said release position.

7. The electrotransfer cassette of claim 1 wherein said upper portion comprises (i) a shell with said pegs and finger grip mounted thereon and (ii) an electrode plate mount joined to said shell by a plurality of slidable mating members, each mating member comprising a resilient hook on one of said shell and said plate mount and an inwardly flanged boss on the to receive said resilient hook.

8. The electrotransfer cassette of claim 7 further comprising a plurality of biasing members on one of said shell and said plate mount to contact the other of said shell and said plate mount, said biasing members compressible to provide a variable spacing between said plate mount and said shell.

9. The electrotransfer cassette of claim 8 wherein said biasing members are coil springs disposed inside said bosses.

10. A method for transferring electrophoretically separated species from a slab gel to a sheet-form matrix, said method comprising:

(a) forming a blotting sandwich defined as a stack comprising said slab gel and said sheet-form matrix, and placing said blotting sandwich between first and second plate electrodes in an electroblotting cassette, said cassette comprising:

(i) an upper portion to which said first plate electrode is mounted and a lower portion to which said second plate electrode is mounted, (ii) a releasable locking mechanism comprising a plurality of pegs movably mounted to said upper portion to move between a locking position in which said pegs engage said lower portion and a release position in which said pegs do not engage said lower portion and said upper and lower portions are free to be separated, and (iii) a finger grip mounted to said upper portion, movable by a single hand of a user to shift all of said plurality of pegs simultaneously between said locking position and said release position, (b) manipulating said finger grip to move said pegs into said locking position, and (c) imposing electrical charges on said first and second plate electrodes to cause said species to migrate electrophoretically within said blotting sandwich from said slab gel to said sheet-form matrix.

11. The method of claim 10 wherein each peg of said plurality of pegs has an axis that is parallel to said first plate electrode and moves along said axis between said locking position and said release position.

12. The method of claim 10 wherein said upper portion of said cassette has a pair of opposing parallel side edges and said plurality of pegs comprise pegs protruding laterally from both said side edges when in said locking position.

13. The method of claim 10 wherein said lower portion of said cassette has raised parallel side edges with apertures positioned to receive said pegs when said pegs are in said locking position.

14. The method of claim 10 wherein said finger grip is rotatable between a first angular position in which said plurality of pegs are in said locking position and a second angular position in which said plurality of pegs are in said release position, and step (b) comprises rotating said finger grip from said second angular position to said first angular position.

15. The method of claim 10 wherein said upper portion of said cassette comprises (i) a shell with said pegs and finger grip mounted thereon and (ii) an electrode plate mount joined to said shell by a plurality of slidable mating members, each mating member comprising a resilient hook on one of said shell and said electrode plate mount and an inwardly flanged boss on the to receive said resilient hook; said blotting sandwich has a thickness; and step (a) comprises lowering said shell over said blotting sandwich while allowing said electrode plate mount to self-adjust in height within said shell to accommodate said thickness when said pegs are in said locking position.

16. The method of claim 15 wherein said upper portion of said cassette further comprises spring-loaded biasing members contacting both said shell and said electro plate mount, and step (a) further comprises compressing said spring-loaded biasing members to cause said cassette to accommodate said thickness when said pegs are in said locking position.

* * * * *